US009464739B2

(12) United States Patent
Chiang et al.

(10) Patent No.: US 9,464,739 B2
(45) Date of Patent: Oct. 11, 2016

(54) GUIDING DEVICE FOR GUIDING A DESPENSER TO DRAW SOLUTION FROM AT LEAST ONE WELL ON A MICROPLATE

(71) Applicant: Wistron Corporation, New Taipei (TW)

(72) Inventors: Chi-Chan Chiang, New Taipei (TW); Ting-Wen Liu, New Taipei (TW); Chih-Kuan Lin, New Taipei (TW); Ya-Hsin Chang, New Taipei (TW)

(73) Assignee: Wistron Corporation, New Taipei (TW)

(*) Notice: Subject to any disclaimer, the term of this patent is extended or adjusted under 35 U.S.C. 154(b) by 434 days.

(21) Appl. No.: 14/084,631

(22) Filed: Nov. 20, 2013

(65) Prior Publication Data

US 2015/0007672 A1 Jan. 8, 2015

(30) Foreign Application Priority Data

Jul. 3, 2013 (TW) .............................. 102123799 A (51) Int. Cl.
*G01N 35/10* (2006.01)
*F16L 25/10* (2006.01)
*B01L 3/00* (2006.01)
*B01L 3/02* (2006.01)

(52) U.S. Cl.
CPC ............ *F16L 25/10* (2013.01); *B01L 3/50853* (2013.01); *G01N 35/1011* (2013.01); *B01L 3/021* (2013.01); *B01L 2200/025* (2013.01); *B01L 2200/026* (2013.01); *B01L 2300/046* (2013.01); *B01L 2300/0829* (2013.01); *G01N 35/1065* (2013.01)

(58) Field of Classification Search
None
See application file for complete search history.

(56) References Cited

U.S. PATENT DOCUMENTS

| 7,597,854 | B1 | 10/2009 | Reynolds | |
|---|---|---|---|---|
| 7,713,487 | B1* | 5/2010 | Locklear et al. | 422/501 |
| 2002/0174878 | A1 | 11/2002 | Nisson | |
| 2010/0229659 | A1* | 9/2010 | Ikushima | 73/864.11 |
| 2011/0253251 | A1* | 10/2011 | Mudd | 141/2 |
| 2014/0050638 | A1* | 2/2014 | Panetz | 422/569 |

FOREIGN PATENT DOCUMENTS

| JP | 200936595 | 2/2009 |
|---|---|---|
| JP | 2010117305 A | 5/2010 |

OTHER PUBLICATIONS

Office action mailed on Aug. 14, 2015 for the China application No. 201310300967.7, p. 3 line 3-31, p. 4-5 and p. 6 line 1.
Office action mailed on Jan. 26, 2015 for the Taiwan application No. 102123799, filing date: Jul. 3, 2013, p. 1 line 10-14, p. 2 line 1-4 and line 7-26 and p. 3 line 1-2.
Office action mailed on Mar. 23, 2016 for the China application No. 201310300967.7, p. 3 line 6-19, p. 4 line 10-30 and p. 5 line 1.

* cited by examiner

*Primary Examiner* — Robert R Raevis
(74) *Attorney, Agent, or Firm* — Winston Hsu; Scott Margo (57) ABSTRACT

The present invention discloses a guiding device for guiding a dispenser to draw solution from at least one well on a microplate. The guiding device includes a column body whereon a first opening and a second opening are formed on opposite sides, and a slotting structure passing through the column body and communicating with the first opening and the second opening. A pipe of the dispenser passes through the first opening, the slotting structure and the second opening to reach inside the at least one well on the microplate for drawing the solution contained in the at least one well.

10 Claims, 9 Drawing Sheets

GUIDING DEVICE FOR GUIDING A DESPENSER TO DRAW SOLUTION FROM AT LEAST ONE WELL ON A MICROPLATE

BACKGROUND OF THE INVENTION

1. Field of the Invention

The present invention is to provide a guiding device, and more specifically, to a guiding device for guiding a dispenser to draw solution from at least one well on a microplate.

2. Description of the Prior Art

It is general to use a dispenser to draw solution from a well on a microplate for an experiment or a test. However, as putting a pipe of the dispenser in a wrong place, it is easy to draw a specimen and the solution at the same time, resulting in affecting an accuracy of the test. For example, when applying a magnetic specimen which the specimen is attracted with iron powder as a carrier, a magnet is often disposed on a lower side of the microplate to attract the magnetic specimen, and then the dispenser can be operated to draw the solution with an automation testing system or an experimenter by visual inspection. However, the solution may not be drawn in a particular angle without drawing the specimen at the same time in a rapid, accurate, easy and low-cost manner. More especially, as there is a huge number of the magnetic specimens to be assayed rapidly and accurately, or as the magnetic specimens disposed in different positions and in different wells on the same microplate have to be assayed, the tests can not be finished rapidly and accurately without an expensive automation testing system. However, in a small laboratory or when lack of funds, it relies on the experience and the physical strength of the experimenters to finish the tests, resulting in inconvenience of the testing process.

SUMMARY OF THE INVENTION

This invention is to provide a guiding device for guiding a dispenser to draw solution from at least one well on a microplate to solve the problems mentioned above.

According to the disclosure, the guiding device for guiding the dispenser to draw solution from the at least one well on the microplate includes a column body whereon a first opening and a second opening are formed on opposite sides, and a slotting structure passing through the column body and communicating with the first opening and the second opening. A pipe of the dispenser passes through the first opening, the slotting structure and the second opening to reach inside the at least one well on the microplate for drawing the solution contained in the at least one well.

According to the disclosure, the slotting structure is substantially not parallel to an axial direction of the column body.

According to the disclosure, the column body is inserted in the at least one well on the microplate.

According to the disclosure, the guiding device further includes a guiding plate whereon at least one hole is formed, the column body is detachably disposed in the at least one hole, and the guiding plate is installed on the microplate.

According to the disclosure, a constraining portion is formed in the at least one hole on the guiding plate, and the column body includes an engaging portion for engaging with the constraining portion so as to constrain a rotation of the column body in the at least one hole on the guiding plate.

According to the disclosure, a plurality of holes is formed on the guiding plate, and the column body is selectively inserted in one of the plurality of holes.

According to the disclosure, the guiding device further includes a guiding plate whereon a hole is formed, the column body is fixed in the hole on the guiding plate, and the guiding plate is installed on the microplate.

According to the disclosure, the guiding device includes a plurality of column bodies separated from or connected with each other.

According to the disclosure, a testing system includes a microplate, at least one magnetic component, a dispenser and a guiding device. A plurality of wells is formed on the microplate for containing solution and magnetic specimens. The at least one magnetic component is disposed on a side of the microplate for attracting the magnetic specimens contained in the plurality of wells. The dispenser includes at least one pipe for drawing solution contained in the plurality of well. The guiding device is for guiding the at least one pipe of the dispenser to draw solution from the plurality of wells on the microplate. The guiding device includes at least one column body, and at least one slotting structure. A first opening and a second opening is formed on opposite sides of each column body. The at least one slotting structure passes through the corresponding column body and communicates with the corresponding first opening and the corresponding second opening, and the at least one pipe of the dispenser passes through the corresponding first opening, the at least one slotting structure and the corresponding second opening to reach inside the corresponding well on the microplate for drawing the solution contained in the corresponding well and for preventing drawing the magnetic specimens contained in the corresponding well.

The present invention provides the guiding device for guiding the pipe of the dispenser to draw the solution in a particular angle without drawing the specimens at the same time in a rapid, accurate, easy and low-cost manner. An experimenter can install the guiding device of the present invention on the microplate easily and rapidly so as to test the whole magnetic specimens or distributed magnetic specimens rapidly and accurately, for enhancing the convenience of the testing process.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
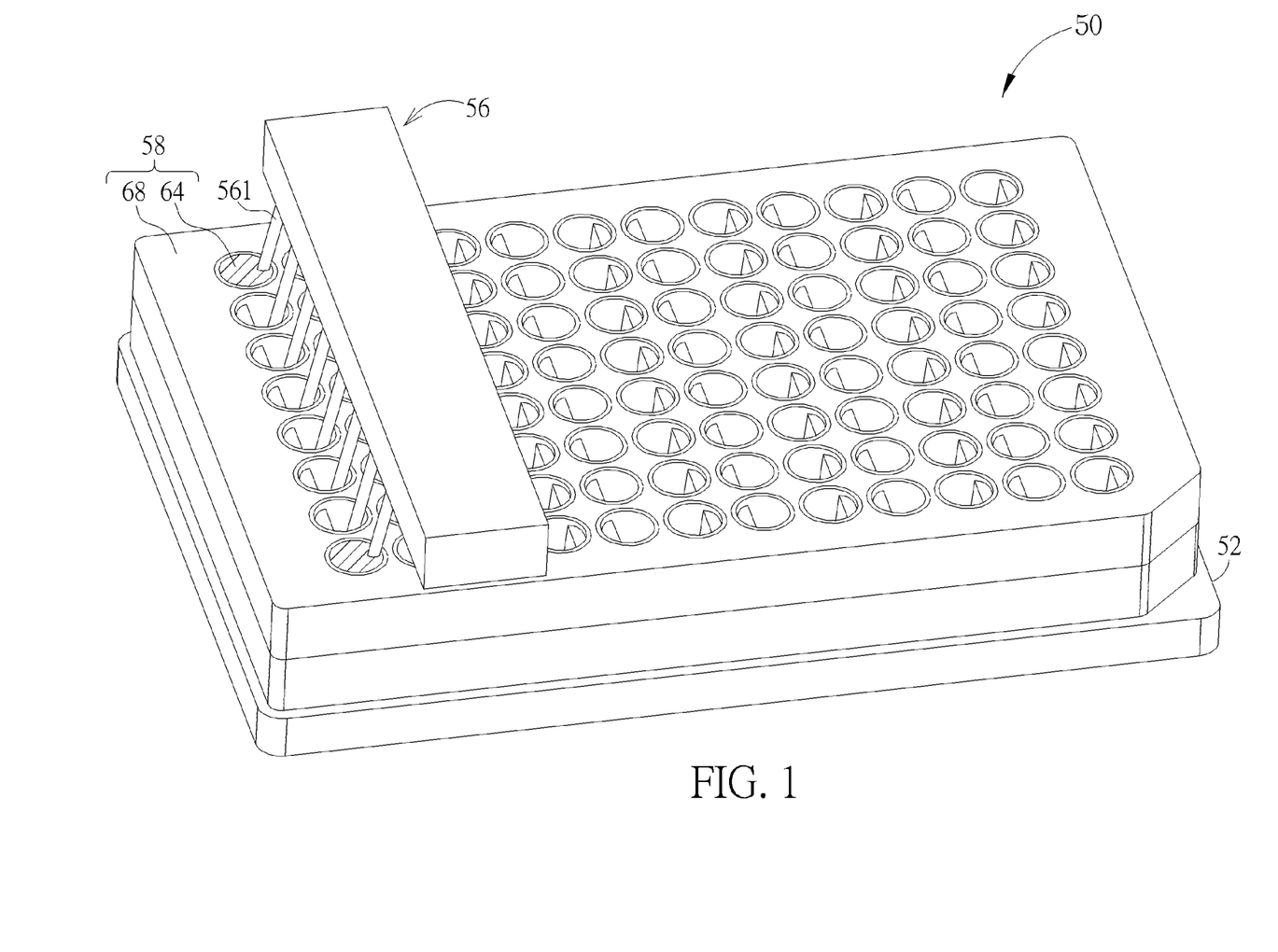
FIG. 1 is a schematic diagram of a testing system according to an embodiment of the present invention.
Figure 2:
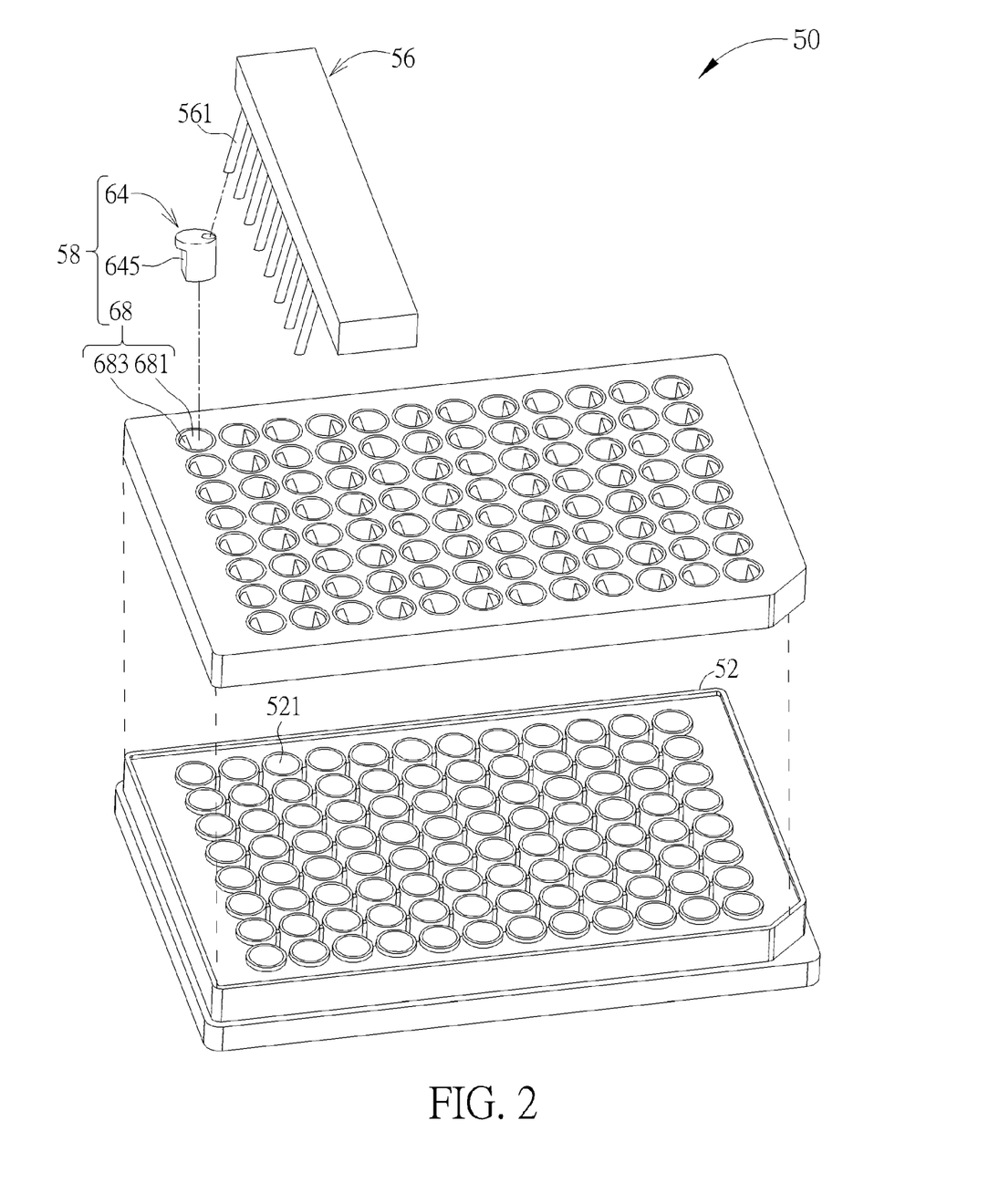
FIG. 2 is an exploded diagram of the testing system according to the embodiment of the present invention.
Figure 3:
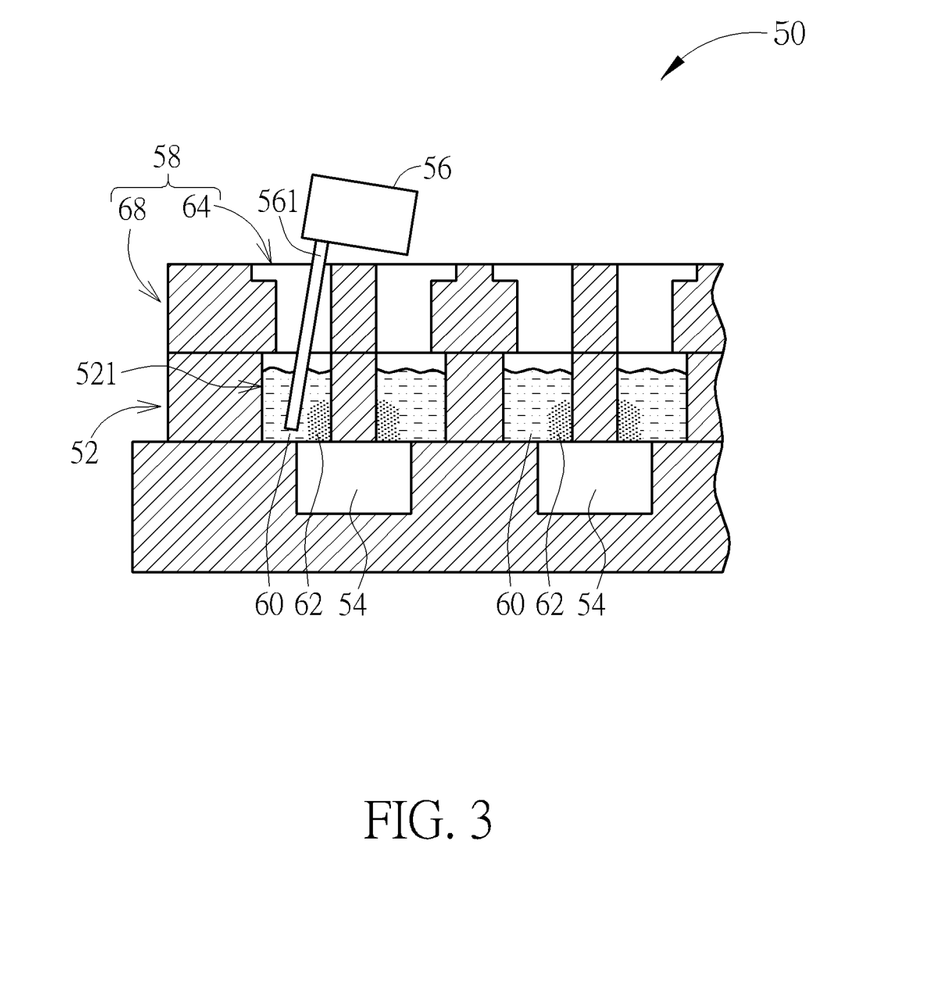
FIG. 3 is a cross-sectional diagram of the testing system according to the embodiment of the present invention.

Please refer to FIG. 1 to FIG. 3. FIG. 1 is a schematic diagram of a testing system 50 according to an embodiment of the present invention. FIG. 2 is an exploded diagram of the testing system 50 according to the embodiment of the present invention. FIG. 3 is a cross-sectional diagram of the testing system 50 according to the embodiment of the present invention. The testing system 50 includes a microplate 52, at least one magnetic component 52, a dispenser 56 and a guiding device 58. A plurality of wells 521 is formed on the microplate 52 for containing solution 60 and magnetic specimens 62. The magnetic component 54 is disposed on a side of the microplate 52 for attracting the magnetic specimens 62 contained in each of the plurality of wells 521, and the magnetic component 54 can be a magnet.

Figure 4:
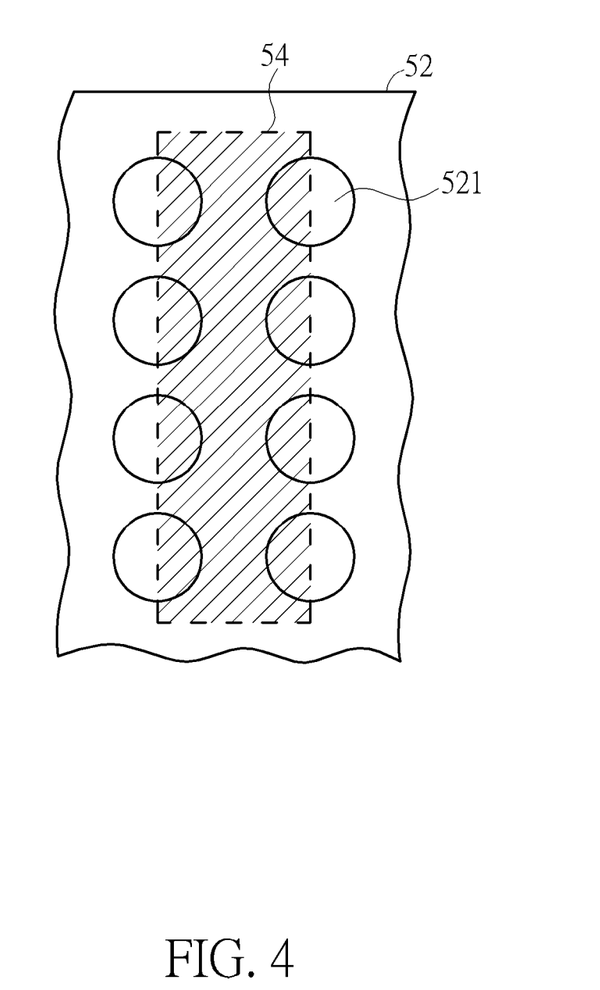
FIG. 4 and FIG. 5 are diagrams illustrating relative positions of at least one magnetic component and at least one well according to different embodiments of the present invention.
Figure 5:
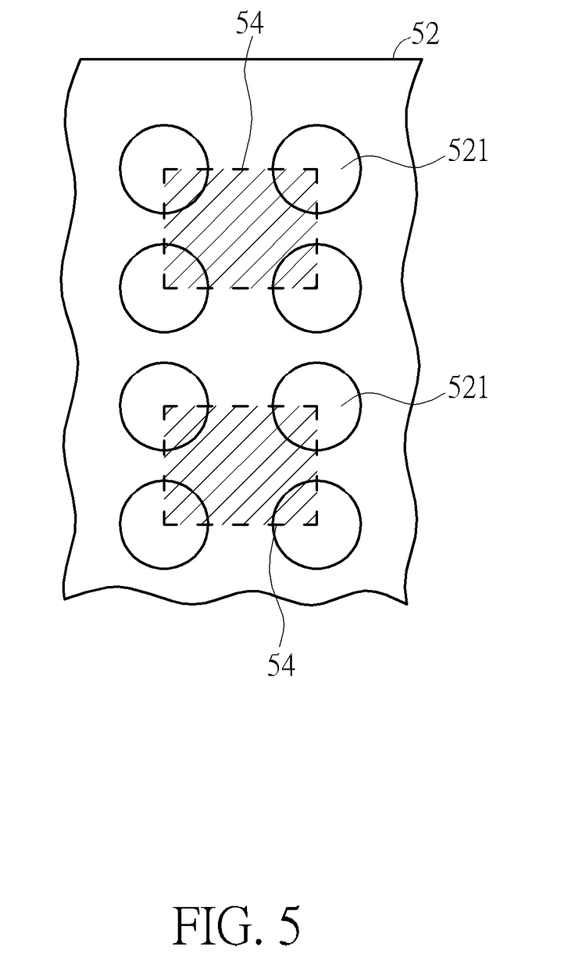

For example, please refer to FIG. 4 and FIG. 5. FIG. 4 and FIG. 5 are diagrams illustrating relative positions of the magnetic component 54 and the plurality of wells 521 according to different embodiments of the present invention. As shown in FIG. 4, two rows of the plurality of wells 521 corresponds to one magnetic component 54. Therefore, the magnetic specimens 62 contained in each of the plurality of wells 521 can be attracted to an inner semicircle of each well 521 close to the magnetic component 54 by the magnetic component 54. Furthermore, as shown in FIG. 5, four wells corresponds to one magnetic component 54, and each magnetic component 54 is disposed in a center of the four wells 521. Therefore, the magnetic specimens 62 contained in each of the plurality of wells 521 can be attracted to a quarter circle of each well 521 close to the magnetic component 54 by the corresponding magnetic component 54. The numbers and the relative positions of the magnet components 54 and the wells 521 are not limited in the above-mentioned embodiment, and a method of utilizing the magnetic component 54 for attracting the magnetic specimens 62 is within the scope of the present invention.

Figure 6:
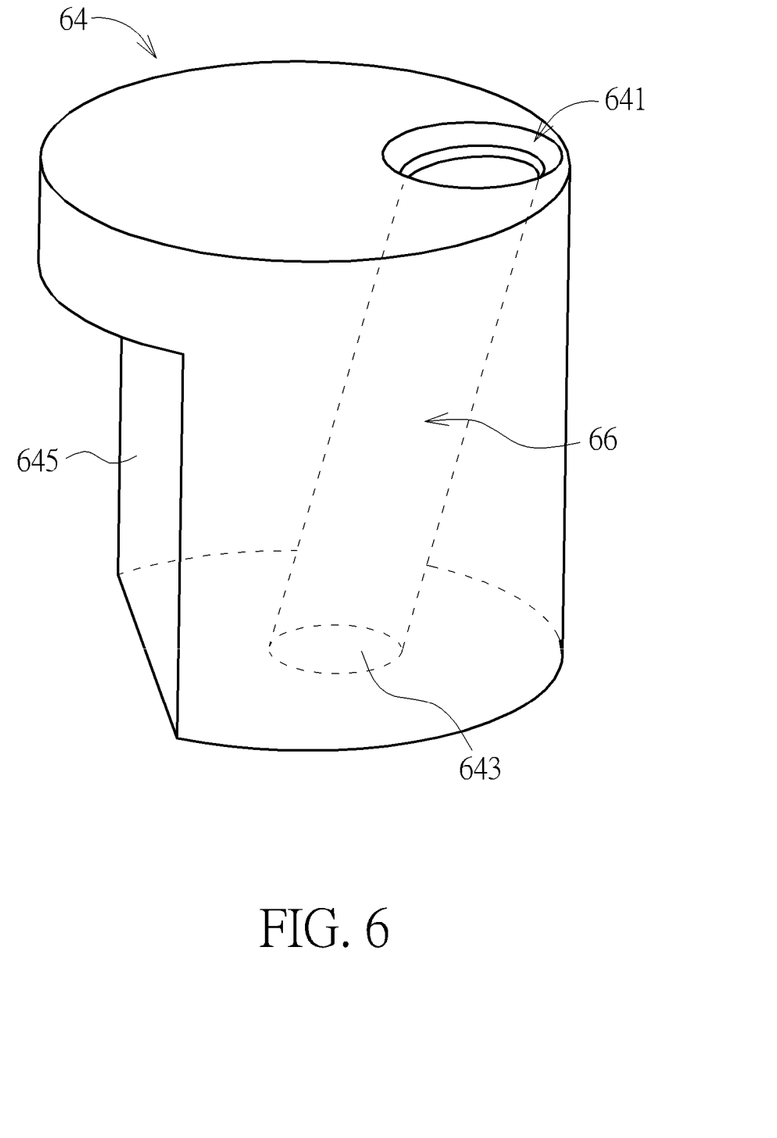
FIG. 6 is a diagram of a column body and a slot slotting structure according to the embodiment of the present invention.

In addition, the dispenser 56 includes at least one pipe 561 for drawing the solution 60 contained in the plurality of wells 521. According to the embodiment, the dispenser 56 includes a plurality of pipes 561 for drawing the solution 60 contained in the plurality of wells 521 on the microplate 52 respectively. The guiding device 58 includes at least one column body 64, and at least one slotting structure 66. Please refer to FIG. 1 to FIG. 6. FIG. 6 is a diagram of the column body 64 and the slotting structure 66 according to the embodiment of the present invention. A first opening 641 and a second opening 643 are formed on two opposite sides of the column body 64. The slotting structure 66 passes through the column body 64 and communicates with the first opening 641 and the second opening 643, the slotting structure 66 can be substantially not parallel to an axial direction of the column body 64. That is, the slotting structure 66 is disposed obliquely. According to this embodiment, the guiding device 58 further includes a guiding plate 68, a plurality of holes 681 is formed on the guiding plate 68, and the column body 64 is detachably selectively inserted in one of the plurality of holes 681. The guiding plate 68 is installed on the microplate 52 so that each of the plurality of holes 681 on the guiding plate 68 is aligned to the corresponding well 521 on the microplate 52. Furthermore, the guiding device 58 can include a plurality of column bodies 64 selectively inserted in the plurality of holes 681. For example, a number of the plurality of column bodies 64 can be equal to a number of the plurality of holes 681. Besides, the number of the plurality of holes 681 can be greater than the number of the plurality of column bodies 64, and the plurality of column bodies 64 is selectively inserted in some of the plurality of holes 681 according to the testing requirement.

Furthermore, a constraining portion 683 is formed in each hole 681 on the guiding plate 68, and the column body 64 includes an engaging portion 645 engaging with the corresponding constraining portion 683, so as to constrain a rotation of the column body 64 in the corresponding hole 681 on the guiding plate 68. That is, the constraining portion 683 is engaged with the engaging portion 645 so that the column body 64 is not able to rotate and the direction of the slotting structure 66 is fixed. Then, the pipe 561 of the dispenser 56 passes through the corresponding first opening 641, the corresponding slotting structure 66 and the corresponding second opening 643 to reach inside the corresponding well 521 on the microplate 52 for drawing the solution 60 contained in the corresponding well 521. As the column body 64 is inserted in the corresponding hole 681 on the guiding plate 68, the column body 64 is not able to rotate in the hole 681 so as to fix the direction of the slotting structure 66, for guiding the pipe 561 of the dispenser 56 to reach inside a particular position in the well 521. Because the magnetic specimens 62 can be attracted by the magnetic component 54, that is, the magnetic specimens 62 are attracted and gathered in a position inside the well 521, the slotting structure 66 can guide the pipe 561 of the dispenser 56 to reach in a position that the magnetic specimens 62 are not gathered inside the well 521, so as to prevent the pipe 561 of the dispenser 56 from drawing the magnetic specimens 62 contained in the corresponding well 521. In conclusion, the column body 64 is utilized to engage with the corresponding hole 681 on the guiding plate 68, and thus the slotting structure 66 guides the pipe 561 of the dispenser 56 to dodge from the position that magnetic specimens 62 are gathered, so as to prevent the pipe 561 of the dispenser 56 from drawing the magnetic specimens 62 contained in the corresponding well 521.

Figure 7:
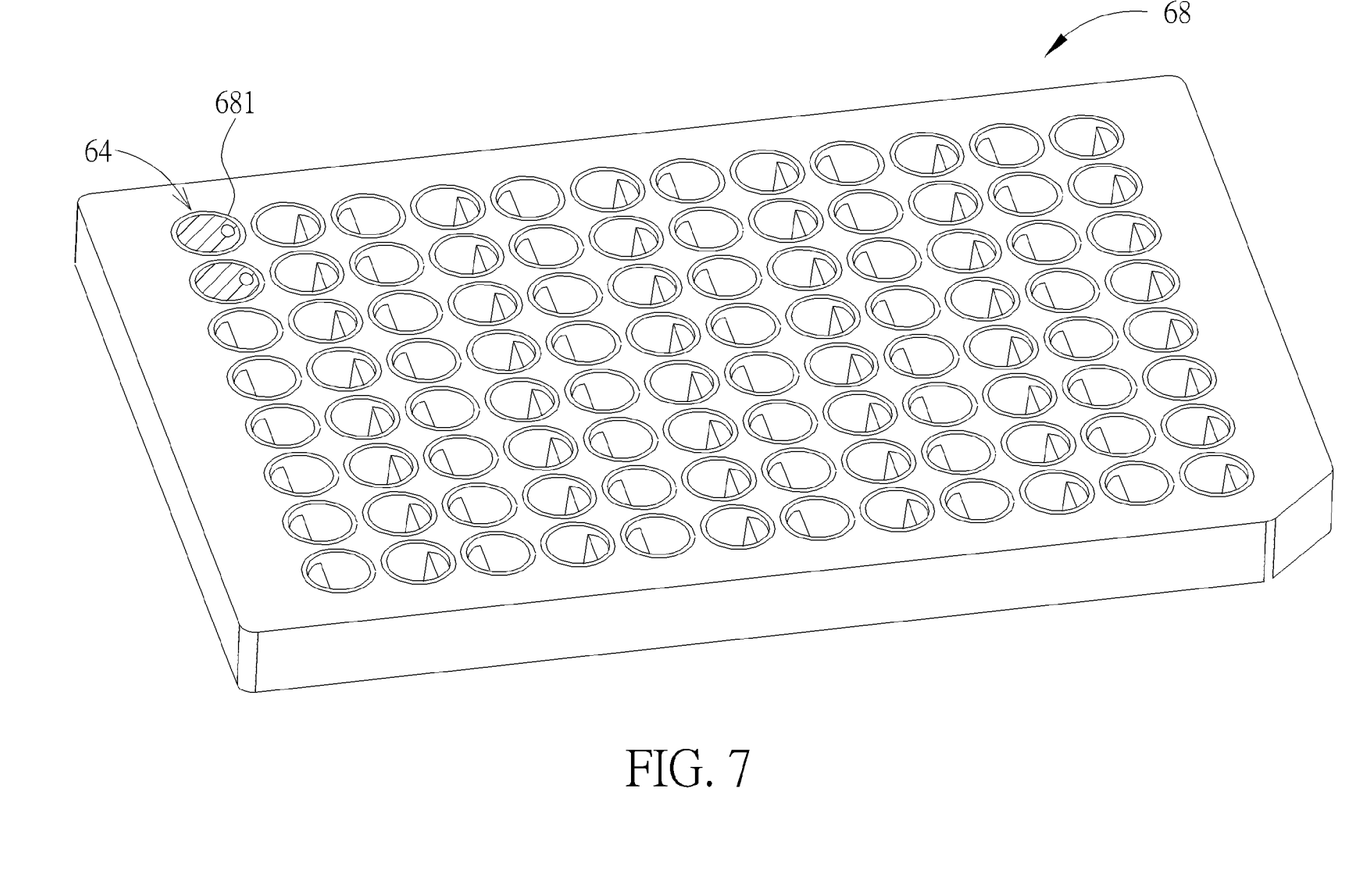
FIG. 7 is a diagram of the column body fixed in a hole on a guiding plate according to another embodiment of the present invention.

In addition, the column body 64 can be undetachably fixed in the hole 681 on the guiding plate 68 directly. Please refer to FIG. 7. FIG. 7 is a diagram of the column body 64 fixed in the hole 681 on the guiding plate 68 according to another embodiment of the present invention. As same as the above-mentioned embodiment, the guiding plate 68 can include the plurality of column bodies 64 selectively fixed in the plurality of holes 681. For example, the number of the plurality of column bodies 64 can be equal to the number of the plurality of holes 681. Or the number of the plurality of holes 681 can be greater than the number of the plurality of column bodies 64, and the plurality of column bodies 64 is selectively fixed in some of the plurality of holes 681. The guiding plate 68 is also installed on the microplate 52 so that each of the plurality of holes is aligned to the corresponding well 521 so that the slotting structure 66 can guide the pipe 561 the dispenser 56. The other operational principle according to this embodiment is similar as the above-mentioned embodiment, and detailed description is not reiterated.

Figure 8:
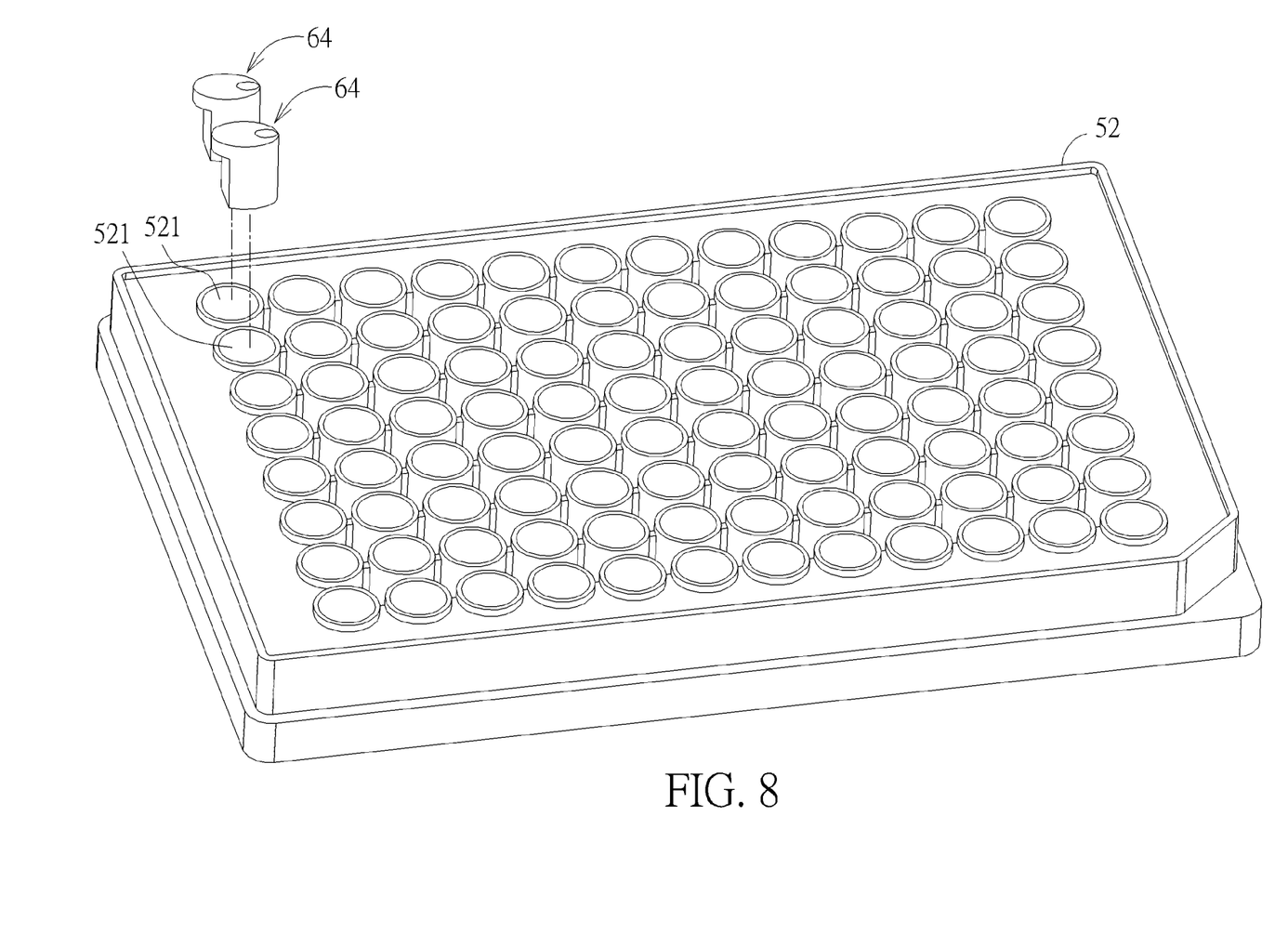
FIG. 8 is a diagram of the column body inserted in a well on a microplate according to another embodiment of the present invention.

Furthermore, the guiding plate 68 can be selectively disposed, it means that the column body 64 can be inserted in the corresponding well 521 on the microplate 52 directly without utilizing the guiding plate 68. Please refer to FIG. 8. FIG. 8 is a diagram of the column body 64 inserted in the corresponding well 52 on the microplate 52 according to another embodiment of the present invention. As same as the above-mentioned embodiment, the guiding device 58 can include the plurality of column bodies 64 selectively inserted in the plurality of wells 521 on the microplate 52. For example, the number of the plurality of column bodies 64 can be equal to the number of the plurality of wells 521. Or the number of the plurality of wells 521 can be greater than the number of the plurality of column bodies 64, and the plurality of column bodies 64 is selectively inserted in some of the plurality of wells 521 so that the slotting structure 66 can guide the pipe 561 of the dispenser 56. The other operational principle according to this embodiment is similar as the above-mentioned embodiment, and detailed description is not reiterated.

Figure 9:
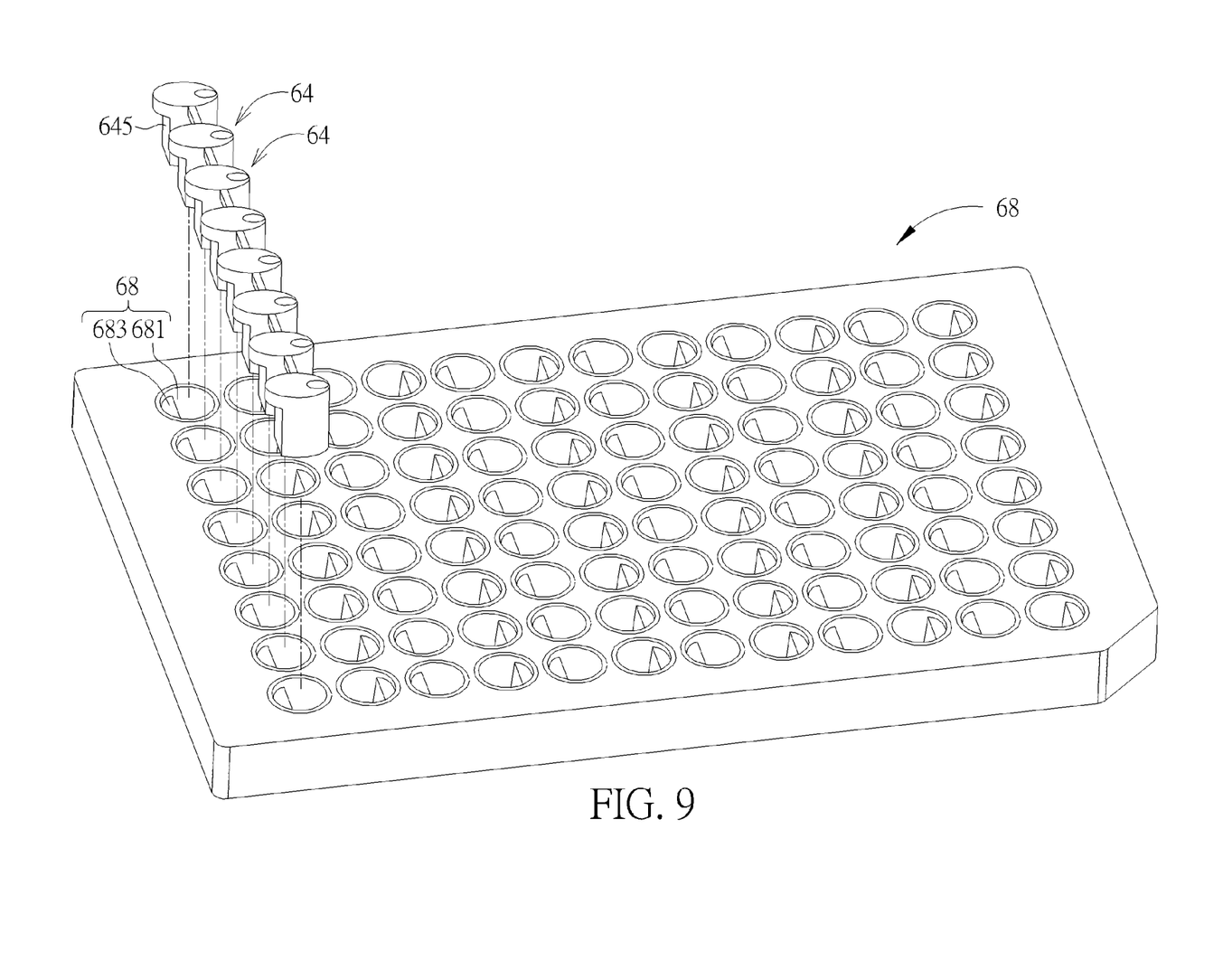
FIG. 9 is a diagram of a plurality of column bodies inserted in a plurality of holes on the guiding plate according to another embodiment of the present invention.

In addition, as the guiding device 58 of the present invention includes the plurality of column bodies 64, the plurality of column bodies 64 can be separately disposed or integrated in a same structure. Please refer to FIG. 9. FIG. 9 is a diagram of the plurality of column bodies 64 inserted in the plurality of holes 681 on the guiding plate 68 according to another embodiment of the present invention. The plurality of column bodies 64 is connected with each other according to this embodiment so as to be integrally inserted in the plurality of holes 681 on the guiding plate 68 at the same time. As same as the above-mentioned embodiment, the number of the plurality of column bodies 64 can be equal to the number of the plurality of holes 681. Or the number of the plurality of holes 681 can be greater than the number of the plurality of column bodies 64, and the plurality of column bodies 64 is selectively inserted in some of the plurality of holes 681 so that the slotting structure 66 can guide the pipe 561 of the dispenser 56. Accordingly, the plurality of column bodies 64 connected to each other can be integrally inserted in the plurality of wells 521 on the microplate 52 at the same time. The other operational principle according to this embodiment is similar as the above-mentioned embodiment, and detailed description is not reiterated.

In contrast to the prior art, the present invention provides the guiding device for guiding the pipe of the dispenser to draw the solution in a particular angle without drawing the specimens at the same time in a rapid, accurate, easy and low-cost manner. An experimenter can install the guiding device of the present invention on the microplate easily and rapidly so as to test the whole magnetic specimens or distributed magnetic specimens rapidly and accurately for enhancing the convenience of the testing process.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A testing system comprising:
a microplate, whereon a plurality of wells are formed for containing solution and magnetic specimens;
at least one magnetic component disposed on a side of the microplate for attracting the magnetic specimens contained in the plurality of wells;
a dispenser comprising at least one pipe for drawing solution contained in the plurality of wells; and
a guiding device for guiding the at least one pipe of the dispenser to draw solution from the plurality of wells on the microplate, the guiding device comprising:
at least one column body, a first opening and a second opening being formed on opposite sides of each column body; and
at least one passageway structure passing through the corresponding column body and communicating with the corresponding first opening and the corresponding second opening, and the at least one pipe of the dispenser passing through the corresponding first opening, the at least one passageway structure and the corresponding second opening to reach inside a corresponding one of the plurality of wells on the microplate for drawing the solution contained in the corresponding one of the plurality of wells and for preventing drawing the magnetic specimens contained in the corresponding one of the plurality of wells.

2. The testing system of claim 1, wherein the at least one passageway structure is substantially not parallel to an axial direction of the at least one column body.

3. The testing system of claim 1, wherein the at least one column body is inserted in the corresponding one of the plurality of wells on the microplate.

4. The testing system of claim 3, wherein the guiding device further comprises a plurality of column bodies for selectively inserting in the plurality of wells.

5. The testing system of claim 1, wherein the guiding device further comprises a guiding plate whereon a plurality of holes are formed, the at least one column body is detachably disposed in a corresponding one of the plurality of holes, and the guiding plate is installed on the microplate.

6. The testing system of claim 5, wherein a constraining portion is formed in each hole on the guiding plate, the at least one column body comprises an engaging portion for engaging with the corresponding constraining portion so as to constrain a rotation of the at least one column body in the corresponding one of the plurality of holes on the guiding plate.

7. The testing system of claim 5, wherein the guiding device comprises a plurality of column bodies for selectively inserting in the plurality of holes.

8. The testing system of claim 1, wherein the guiding device further comprises a guiding plate whereon a plurality of holes are formed, the at least one column body is fixed in a corresponding one of the plurality of holes on the guiding plate, and the guiding plate is installed on the microplate.

9. The testing system of claim 8, wherein the guiding device comprises a plurality of column bodies being selectively fixed in the plurality of holes.

10. The testing system of claim 1, wherein the guiding device comprises a plurality of column bodies separated from or connected with each other.

* * * * *